United States Patent [19]
Young et al.

[11] Patent Number: 5,234,906
[45] Date of Patent: Aug. 10, 1993

[54] HYPERGLYCEMIC COMPOSITIONS

[75] Inventors: Andrew Young, San Diego; Garth J. S. Cooper, Solana Beach, both of Calif.

[73] Assignee: Amylin Pharmaceuticals, Inc., San Diego, Calif.

[21] Appl. No.: 640,478

[22] Filed: Jan. 10, 1991

[51] Int. Cl.$^5$ ............................................. A61K 37/28
[52] U.S. Cl. ........................................ 514/12; 514/21
[58] Field of Search ................... 514/12, 21, 808, 866, 514/884

[56] References Cited

U.S. PATENT DOCUMENTS 4,826,763  5/1989  Norris et al. ........................ 435/69.4

FOREIGN PATENT DOCUMENTS 309100  3/1989  European Pat. Off. .

OTHER PUBLICATIONS

Leighton et al, "Pancreatic Amylin and Calcitonin Gene-Related Peptide Cause Resistance to Insulin . . . ", Nature 335: 632–35 (1988).
Yamaguchi et al, "Calcitonin Gene-Related Peptide and Induction of Hyperglycemia . . . ", Diabetes 39: 168–74 (Feb. 1990).
Molina et al, "Induction of Insulin Resistance In Vivo by Amylin and CGRP", Diabetes 39: 260–65 (Feb. 1990).
Cooper et al., Biochem. Biophys. Acta 1014:247–58 (1989).
Cooper et al., Proc. Nat'l. Acad. Sci., USA 85:7763–66 (1988).
Leighton et al., Diab. Med. 6: Suppl. 2, A14 (1989).
Ciraldi et al., Diabetes 39:149A (1990).
Kreutter et al., Diabetes 39:121A (1990).
Molina et al., Diabetes 39:260–65 (1990).
Koopmans et al., Diabetes 39:101A (1990).
Young et al., Diabetes 39:116A (1990).
V. Marks, "Glucagon in the Diagnosis and Treatment of Hypoglycemia," Chapter 55 of Handbook of Experimental Pharmacology, vol. 66/II, P. J. Lefebvre (Ed.) (Springer-Verlag 1983).
Young et al., Am. J. Physiol. 259:E457–61 (1990).
Leighton et al., Biochem. J. 269—19-23 (1990).
Yamaguchi et al. Diabetes 39:168–74 (1990).
Leighton et al., TIBS 15:295–99 (1990).
Ahren et al., Int'l. Journal of Pancreatology 6:1–15 (1990).
Nishi et al., Journal of Biological Chemistry 265:4173–76.
Clark, Diab. Med. 6:561–67 (1989).
Cooper et al., Diabetes 1988, pp. 493–496, Larkins, Zimmet, and Chisholm (Eds.), (Elsevier Science Publishers B.V. 1989).
Cooper et al., Progress in Growth Factor Research 1:99–105 (1989).
Johnson et al., New England Journal of Medicine 321:513–18 (1989).

Primary Examiner—Jeffrey E. Russel
Attorney, Agent, or Firm—Lyon & Lyon

[57] ABSTRACT

Compositions having amylin or an amylin agonist and a glucagon compound, particularly peptide compounds, for the control of glucose production in mammals are provided. The compositions are useful in the treatment of hypoglycemia, including acute hypoglycemic conditions such as those brought on by insulin overdose and the overuse of oral hypoglycemic agents.

24 Claims, 7 Drawing Sheets

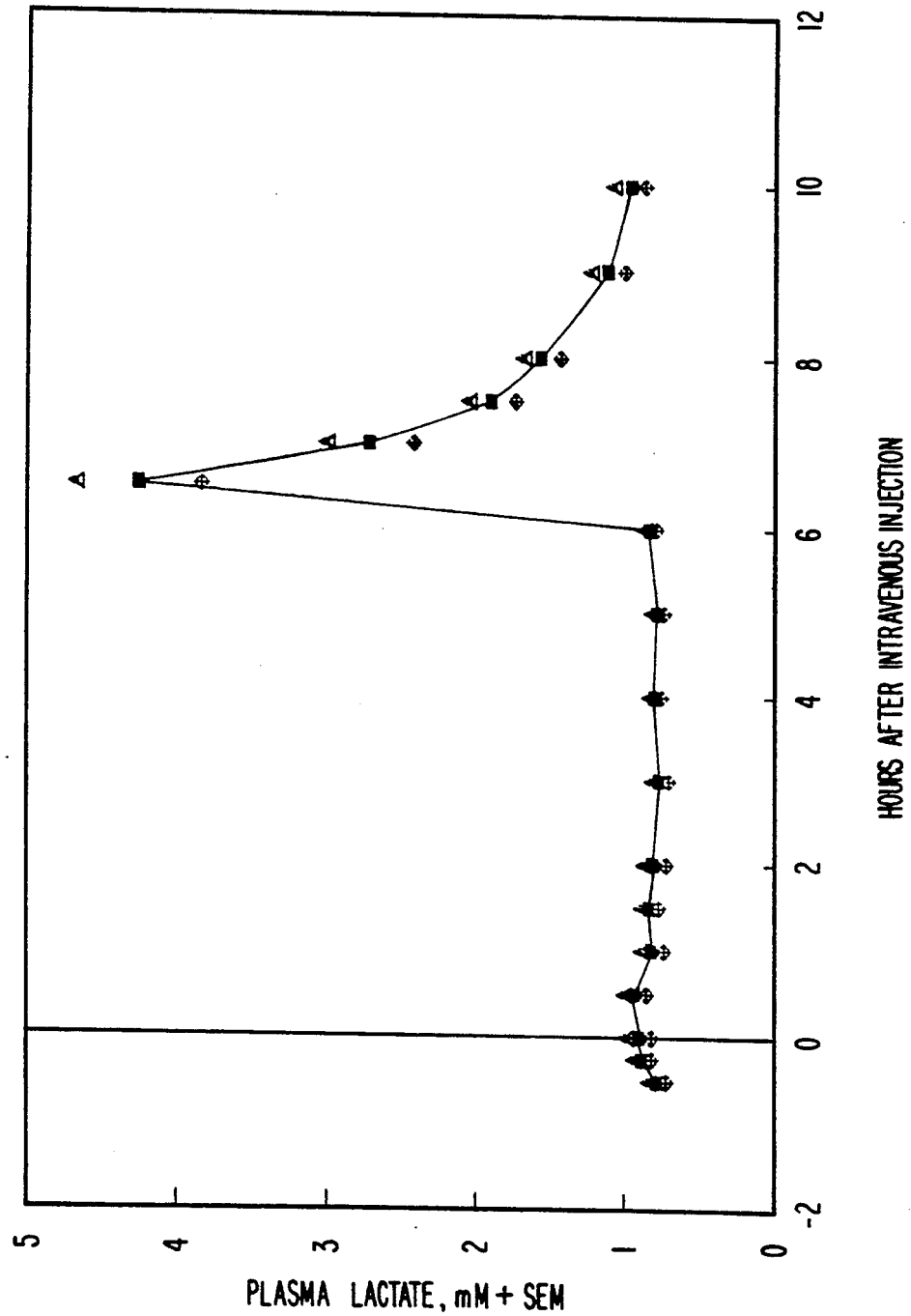

HYPERGLYCEMIC COMPOSITIONS

FIELD OF THE INVENTION

The field of the invention is biology and, more particularly, the biology of diabetes. The invention relates to compositions which comprise amylin or an amylin agonist and a glucagon compound, which are preferably polypeptides, for use in the treatment of acute hypoglycemia and other hypoglycemic conditions.

BACKGROUND

Glucagon was discovered in 1923, two years after the discovery of insulin. Chemically unrelated to insulin, glucagon is a single-chain polypeptide hormone containing 29 amino acid residues and having a molecular weight of nearly 3500. In contrast to insulin, glucagon contains no cysteine and, consequently, no disulfide linkages. The structure of human glucagon is identical to porcine, bovine, and rat glucagon and many current glucagon preparations are extracted from beef and pork pancreas.

Glucagon secretion, like that of insulin, is controlled by the interplay of gastrointestinal food products, hormones, and other factors. Glucagon is secreted from pancreatic α-cells in response to stimuli which include (i) falling blood glucose levels, (ii) the physiological increments in amino acids which follow a protein meal, (iii) vigorous exercise, (iv) starvation, and (v) hypoglycemia. It was discovered as a hyperglycemic factor, present in pancreatic extracts, which stimulated hepatic glycogenolysis (the so-called 'hyperglycemic glycogenolytic factor'). Glucagon is reported to exert major effects on liver glucose metabolism to increase hepatic glucose production, at least through cAMP-mediated actions, which are exerted both directly, to release glucose from glycogen through stimulation of glycogenolysis, and indirectly, through inhibition of glycogen synthesis. During relative hypoinsulinemia, glucagon can also stimulate gluconeogenesis. Glucagon is not considered to exert physiologically significant effects on carbohydrate metabolism in muscle.

Glucose is physiologically the most important regulator of glucagon. A rise in plasma glucose concentration leads to an inhibition of glucagon secretion and vice versa. Unger, R. H. and Orci, L., "Glucagon and the A Cell," N. Eng. J. Med. 304:1518-1524 and 1575-1580 (1981). Both insulin and somatostatin inhibit the secretion of glucagon.

The role of glucagon and, in general, its actions are reported to be antagonistic to those of insulin. Insulin serves as a hormone of fuel storage while glucagon is reported to serve as a hormone of fuel mobilization. Following a carbohydrate meal, pancreatic β-cells secrete insulin and pancreatic α-cell secretion of glucagon is suppressed; this allows cells to store fuels such as glucose in liver, muscle, and adipose tissue. Conversely, during starvation, stimulation of glucagon secretion and suppression of insulin secretion direct breakdown and efficient utilization of fuels stored intracellularly, initially liver glycogen, and subsequently adipose tissue fat, to meet the energy needs of the brain and other tissues. A regulated role for glucagon as the hormone of injury and insult (catabolic illness) has been proposed. For example, impaired glucose tolerance and hyperglycemia noted with infection are associated with increased concentrations of plasma glucagon. Similar increases are seen in patients with myocardial infarctions, burns, and after major trauma. In these situations, glucagon is said to stimulate gluconeogenesis and provide the glucose needed under conditions of insult.

Glucagon, therefore, has generally accepted physiological roles as a counterregulatory (anti-hypoglycemic) hormone, and a major regulator of fuel metabolism during starvation. Because of its effect to increase blood glucose levels in individuals with extant hepatic glycogen stores, glucagon is widely used clinically in the acute management of severe hypoglycemia complicating insulin replacement therapy of insulin-dependent (type 1) diabetes mellitus. Glucagon is particularly useful in the treatment of insulin-induced hypoglycemia when dextrose (glucose) solution is not available or, for example, when a patient is convulsing or recalcitrant and intravenous glucose cannot be administered. Glucagon is effective in small doses, and no evidence of toxicity has been reported with its use.

When given, glucagon may be administered intravenously, intramuscularly, or subcutaneously, typically in a dose of 1 milligram. Once glucagon is introduced for hypoglycemic coma induced by either insulin or oral hypoglycemic agents, a return to consciousness should be observed within 20 minutes; otherwise, intravenous glucose must be administered as soon as possible. *Goodman and Gillman's The Pharmacolooic Basis of Theraueutics*, p. 1510-1512 (7th Ed. 1985).

Hypoglycemic reactions may occur in any diabetic subject treated with insulin or with an oral hypoglycemic agent. Reactions are frequently seen in the labile form of the disease, a form characterized by unpredictable spontaneous reductions in insulin requirement. In other instances, precipitating causes are responsible, such as a failure to eat, unaccustomed exercise, and inadvertent administration of too large a dose of insulin. Frequently, however, there is no discernible cause. When the rate of fall in blood glucose is rapid, the early symptoms are those brought on by the compensating secretion of epinephrine, which includes sweating, weakness, hunger, tachycardia, and "inner trembling." When the concentration of glucose falls slowly, the symptoms and signs are primarily related to the brain and include headache, blurred vision, diplopia, mental confusion, incoherent speech, coma, and convulsions. If the fall in blood glucose is rapid, profound, and persistent, all such symptoms may be present.

The majority of the signs and symptoms of insulin hypoglycemia are the results of functional abnormalities of the central nervous system, since hypoglycemia deprives the brain of the substrate (glucose) upon which it is almost exclusively dependent for its oxidative metabolism. During insulin coma, oxygen consumption in human brain decreases by nearly half. The reduction in glucose consumption is disproportionately greater, which indicates that the brain is utilizing other substrates. After prolonged fasting in man the brain adapts, and the bulk of the fuel utilized is made up of ketone bodies. A prolonged period of hypoglycemia causes irreversible damage to the brain. *Goodman and Gillman's The Pharmacologic Basis of Therapeutics*, p. 1502-1503 (7th Ed. 1985).

The symptoms of hypoglycemia yield almost immediately to the intravenous injection of glucose unless hypoglycemia has been sufficiently prolonged to induce organic changes in the brain. If the patient is not able to take a soluble carbohydrate or a sugar-containing liquid such as fruit juice orally and if glucose is not available for intravenous injection, glucagon may be given. It will be understood, however, that the utility of glucagon in treating hypoglycemia is limited by its inaction or ineffectiveness in patients with depleted liver glycogen stores. Since glucagon acts only on liver (but not on skeletal muscle) glycogen by converting it to glucose, it has no therapeutically useful hyperglycemic effect in patients with depleted liver glycogen, a condition which cannot be determined in the fitting patient. Thus, in the convulsing or comatose patient, glucagon treatment will not alleviate hypoglycemia if the patient has no or insufficient liver glycogen to be mobilized. In addition to states of starvation, it is also understood that glucagon is of little or no help in other states in which liver glycogen is depleted such as adrenal insufficiency or chronic hypoglycemia. Normally, then, intravenous glucose must be given if the patient fails to respond to glucagon.

SUMMARY OF THE INVENTION

The present invention is directed to methods of controlling glucose production in mammals, and to methods of treating acute hypoglycemia and other hypoglycemic conditions, by the co-administration of a glucagon compound and amylin or an amylin agonist. In particular, the method comprises the administration of a preferred composition comprising a combined glucagon and amylin pharmaceutical composition for treatment of hypoglycemic conditions. These compositions are particularly useful in treating those hypoglycemic conditions where the effect of glucagon or amylin alone may not be predicted with certainty. In instances of severe hypoglycemia, especially with an unconscious or comatose patient or animal, it is important to reliably alleviate hypoglycemia without the necessity of inquiry into nutritional status or the presence or absence of hepatic glycogen stores.

The invention also provides for pharmaceutical compositions comprising a glucagon compound and amylin or an amylin agonist together in a pharmaceutically acceptable carrier in therapeutically effective amounts.

BRIEF DESCRIPTION OF THE DRAWINGS

The invention will be further described with reference to the accompanying drawings in which:

FIGS. 5A and 5B show the effects of an intravenous injection of 100 micrograms glucagon (0 hours) followed by an intravenous injection of 100 micrograms amylin (6 hours) on plasma arterial levels of glucose (5A) and lactate (5B) in 18-hour fasted rats.

DETAILED DESCRIPTION OF THE INVENTION

Figure 1:
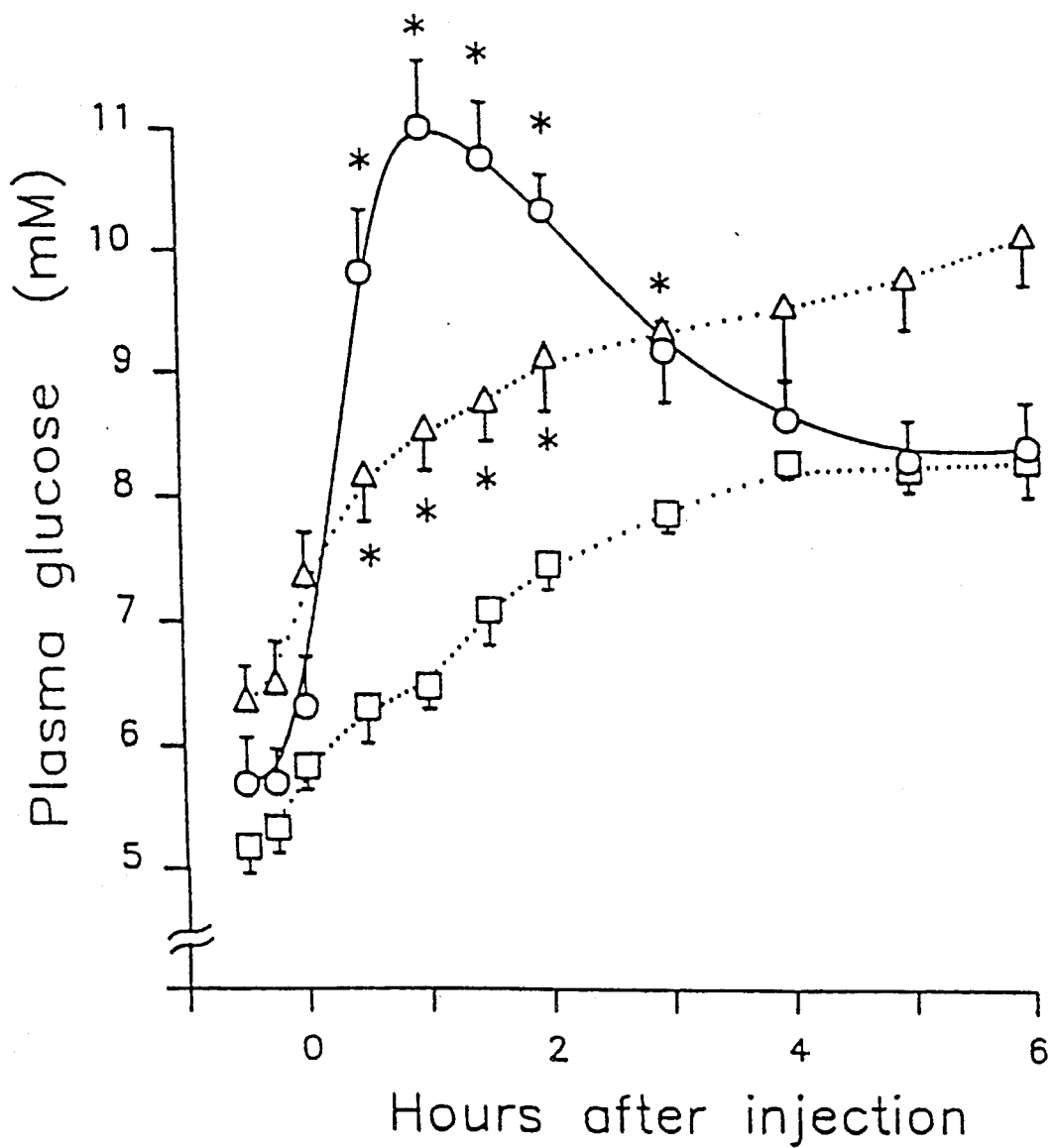
FIG. 1 shows the plasma glucose response (mean±SEM, n=6 for each curve) of rats infused with somatostatin (3.4 nmol/hr) and injected with 66 nmol/kg amylin (open circle), peptide control (open square), or phentolamine in a regimen that replicated the blood pressure response to amylin (BP control, open triangle). Asterisks above the symbols indicate differences between amylin-treated and peptide control groups. Asterisks below the symbols indicate differences between the amylin treated and BP control groups.

Diabetes mellitus is a metabolic disorder which is defined by the presence of chronically elevated levels of blood glucose (hyperglycemia). Dietary carbohydrate is absorbed into the bloodstream mainly in the form of glucose. The pancreatic hormone insulin stimulates the rapid clearance of glucose from the blood by stimulating glucose oxidation, the conversion of glucose to glycogen in skeletal muscle and triacylglycerol in liver and adipose tissue and also by suppression of hepatic glucose production. Insulin, therefore, plays a fundamental role in maintaining blood glucose levels within the physiological range.

Insulin-dependent (Type 1) diabetes mellitus ("IDDM") results from an autoimmune-mediated destruction of pancreatic $\beta$-cells with consequent loss of insulin production, which results in hyperglycemia. People with Type 1 diabetes have an absolute requirement for insulin replacement therapy in order to ensure survival. In marked contrast, non-insulin-dependent (Type 2) diabetes mellitus ("NIDDM") is often characterized by hyperglycemia in the presence of higher-than-normal levels of plasma insulin (hyperinsulinemia). Thus, in Type 2 diabetes, tissue processes which control carbohydrate metabolism are believed to have decreased sensitivity to insulin. Progression of the Type 2 diabetic state is associated with increasing concentrations of blood glucose and coupled with a relative decrease in the rate of glucose-induced insulin secretion.

The primary aim of treatment in both forms of diabetes mellitus is the same, namely, the reduction of blood glucose levels to as near normal as possible. The treatment of Type 1 diabetes necessarily involves the administration of replacement doses of insulin, which is administered by the parenteral route. In contrast, the treatment of Type 2 diabetes frequently does not require the administration of insulin. For example, initial therapy of Type 2 diabetes may be based on diet and lifestyle changes augmented by therapy with oral hypoglycemic agents such as the sulfonylureas. If after an adequate trial of diet and lifestyle modification, fasting hyperglycemia persists in the Type 2 diabetic patient, a diagnosis of "primary diet failure" may be made, and either a trial of oral hypoglycemic therapy or direct institution of insulin therapy may be required to produce control of hyperglycemia in an attempt to minimize the complications of the disease.

Treatment with oral hypoglycemic agents such as the sulfonylureas may lead to hypoglycemic reactions, including coma, four or more hours after meals. These hypoglycemic episodes may last for several days so that prolonged or repeated glucose administration is required. Such hypoglycemic reactions are unpredictable and may occur after as little as one dose, after several days of treatment, or after months of drug administration. Most hypoglycemic reactions are observed in patients over 50 years of age, and are most likely to occur in patients with impaired hepatic or renal function. Over-dosage or inadequate or irregular food intake may initiate such hypoglycemic reactions. Other drugs can increase the risk of hypoglycemia from sulfonylureas; these include other hypoglycemic agents, sulfonamides, propranolol, salicylates, phenylbutazone, probenecid, dicumarol, choloramphenacol, monoamine oxidase inhibitors, and alcohol.

It is noteworthy that, notwithstanding the above-noted avenues of treatment, insulin therapy remains a treatment of choice for many patients with Type 2 diabetes, especially those who have undergone primary diet failure and are not obese or those who have undergone both primary diet failure and secondary oral hyperglycemic failure. Nevertheless, insulin therapy must be combined with a continued effort at dietary control and lifestyle modification, and in no way can be thought of as a substitute for these. In order to achieve optimal results, insulin therapy should be combined with self blood glucose monitoring and appropriate estimates of glycosylated blood proteins.

As with the sulfonylurea agents, hypoglycemia is the major adverse effect of insulin therapy and is a primary factor preventing the achievement of euglycemic control in the insulin therapy of Type 1 diabetes. Hypoglycemia is by far the most serious and common adverse reaction to the administration of insulin, and can result in substantial morbidity and even death. Thus, it will be understood that the major barrier in striving for euglycemia with intensified regimens of insulin treatment is the increased risk of severe hypoglycemia. Zinman, B., "The Physiologic replacement of insulin. An elusive goal," *N.Engl. J. Med.*, 321:363-370 (1989).

Insulin-induced hypoglycemia is experienced at some time by virtually all Type 1 diabetics. In some studies, severe hypoglycemia (necessitating hospitalization or assistance from another person) has been observed in 25% of all diabetic patients over a one year period. In addition, hypoglycemia is reported to account for about 3-7% of deaths in patients with Type 1 diabetes. Shafrir, E., et al. in Felig, P., et al., "Endocrinology and Metabolism," pages 1043-1178 (2nd edition 1987). Although rates of hypoglycemic incidents vary among individuals, patients undergoing conventional insulin therapy suffer an average of about one episode of symptomatic hypoglycemia per week, whereas those practicing intensive insulin therapy suffer about two to three such episodes per week. Thus, over a time frame of forty years of Type 1 diabetes, the average patient can be projected to experience two thousand to four thousand episodes of symptomatic hypoglycemia. Approximately 10% of patients undergoing conventional insulin therapy suffer at least one episode of severe hypoglycemia, i.e., requiring assistance from others, including hyperglycemic treatment such as glucose or glucagon administration and episodes with seizure or loss of consciousness, in a given year. The yearly incidence of severe hypoglycemic episodes rises to about 25% among patients undergoing intensive therapy. Cryer, P. E., et al., "Hypoglycemia in IDDM" *Diabetes* 38:1193-1198 (1989).

The brain has only an extremely limited ability to store carbohydrate in the form of glycogen and is almost entirely dependent on glucose as its source of energy; thus, it is very sensitive to hypoglycemia. Hypoglycemia is defined as a blood-glucose level of below 40 mg/ml; symptoms of cerebral dysfunction rarely occur until the glucose content of the cerebral arterial blood falls below this level. However, symptoms of hypoglycemia may occur even though the blood-glucose is normal or only minimally reduced, if there has been a rapid fall from a much higher level. Severe or recurrent episodes of hypoglycemia may result in permanent cerebral damage. Thus, treatment of the hypoglycemic state represents a medical emergency.

Amylin is the major protein constituent of the islet amyloid which is reported to be found in patients with type 2 diabetes mellitus. Human amylin has a somewhat unusual amino acid composition in that it contains no acidic residues. Amylin is a 37 amino acid peptide having two post translational modifications, a $Cys^2$-$Cys^7$ intramolecular disulfide bond and a carboxy-terminal amide group. It has been reported that the presence of both of these post-translational modifications in the peptide structure of the synthetic molecule yield the greatest biological activity to inhibit glycogen synthesis in skeletal muscle. Cooper, G. J. S., Willis, A. C., Clark, A., Turner, R. C., Sim, R. B. & Reid, K. B. M. *Proc. Natl. Acad. Sci.* USA 84:8628-8632 (1987); Cooper, G. J. S., Roberts, A. N., Todd, J. A., Sutton, R., Day, A. J., Willis, A. C., Reid, K. B. M. & Leighton, B. in Diabetes 1988, ed. Larkins, R., Zimmet, P. & Chisholm, D. (Elsevier, Amsterdam), pp. 493-496 (1989).

Human amylin has 43-46% sequence identity with human CGRP-1 and CGRP-2 (calcitonin gene-related peptides 1 and 2) respectively. Human amylin also has weaker sequence similarities with calcitonin, insulin, the relaxins, and the insulin-like growth factors (IGFs). This observation concerning sequence similarities supports the determination that there is a peptide hormone superfamily which includes calcitonin, the CGRPs, amylin, and the A-chain related region of the relaxin, insulin and the IGFs. Amylin is reported to be the product of a single gene present on chromosome 12 in humans. This gene has typical features of one encoding a polypeptide hormone, including prepro- and proamylin sequences, typical 5' and 3' dibasic processing signals, and a Gly residue 3' to the codon for the carboxyterminal Tyr, which constitutes an amidation signal. Roberts, A. N., et al., *Proc. Nat. Acad. Sci.* U.S.A. 86:9662-9666 (1989). There is a high degree of interspecies conservation between both the amylins and the CGRPs, particularly in the region of the amino- and carboxy-termini. These regions of strong conservation correspond to the structural regions within the molecules which contain the post-translational modifications necessary for at least some of their biological activities. The variable sequence in the mid-portion of the amylin molecule contains the region said to be primarily responsible for amyloid formation.

Amylin is synthesized in the islets (Leffert, J. D., Newgard, C. B., Okamoto, H., Milburn, J. L. & Luskey, K. L, *Proc. Natl. Acad. Sci.* USA 86:3127-3130 (1989) and Roberts, A. N., Leighton, B., Todd, J. A., Cockburn, D., Sutton, R., Boyd, Y., Holt, S., Day, A. J., Foot, E. A., Willis, A. C., Reid, K. B. M. & Cooper, G.

J. S., *Proc. Natl. Acad. Sci. USA* 86:9662-9666 (1989)), from which it is secreted along with insulin in response to nutrient secretagogues. Ogawa, A., Harris, V., McCorkle, S. K., Unger, R. H. & Luskey, K. L., *J. Clin. Invest.* 85, 973-976 (1990). Deposition of amylin in islet amyloid correlates well with the loss of islet β-cells and defective insulin secretion found in type 2 diabetics. Gepts, W., *The Islets of Lanoerhans*, ed. Cooperstein, S. J. & Watkins, D. (Academic Press, New York, NY), pp. 321-356 (1980), Fehmann, H. C., Weber, V., Goke, R., Goke, B. & Arnold, R., *FEBS Lett.* 262:279-281 (1990) and Cooper, G. J. S., Day, A. J., Willis, A. C., Roberts, A. N., Reid, K. B. & Leighton, B., *Biochim. Biophys. Acta* 1014, 247-258 (1989). Amylin's ability to cause insulin resistance in many model systems, combined with its presence in human islet amyloid, supports the determination that it is central to the pathogenesis of non-insulin dependent diabetes mellitus. Cooper, G. J. S., Day, A. J., Willis, A. C., Roberts, A. N., Reid, K. B. & Leighton, B. *Biochim. Biophys. Acta* 1014:247-258 (1989) and Leighton, B. & Cooper, G. J. S., *Nature* (Lond) 335:632-635 (1988).

In skeletal muscle in vitro, amylin has been reported to modulate several key pathways of carbohydrate metabolism, including incorporation of glucose into glycogen (Leighton, B. & Cooper, G. J. S., *Nature* (Lond) 335:632-635 (1988) and Cooper, G. J. S., Leighton, B., Dimitriadis, G. D., Parry-Billings, M., Kowalchuk, J. M., Howland, K., Rothbard, J. B., Willis, A. C. & Reid, K. B. M., *Proc. Natl. Acad. Sci. USA* 85:7763-7766 (1988)), glycogenolysis (Leighton, B., Foot, E. A. & Cooper, G. J. S. (1989) *Diab. Med.* 6: Suppl. 2, A4 (1989)), and glucose uptake. Ciaraldi, T. P., Cooper, G. J. S. & Stolpe, M., *Diabetes* 39, 149A. (1990) and Kreutter, D., Orena, S. J. & Andrews, G. C., *Diabetes* 39, (Suppl. 1):121A (1990). The effects of amylin in skeletal muscle depend upon distribution of fiber type. Leighton, B., Foot, E. A. & Cooper, G. J. S. (1989) *Diab. Med.* 6: Suppl. 2, A4 (1989). While amylin was reported to inhibit glycogen synthesis in both red (soleus) and white (extensor digitorum longus) muscle, it was reported to stimulate glycogenolysis (and subsequent lactate production) only in white muscle. Leighton, B., Foot, E. A. & Cooper, G. J. S., *Diab. Med.* 6, Suppl. 2:A4 (1989). White (type II) muscle fibers constitute the bulk of muscle mass in most mammals surveyed. Ariano, M. A., R. B. Armstrong, and V. R. Edgerton, *J. Histochem. Cytochem.* 21:51-55 (1973).

The effects of amylin on glycogen synthesis in isolated red muscle (soleus) were reported equipotent with those of the pure β-adrenergic agonist, isoprenaline. Leighton, B. & Cooper, G. J. S., *Nature* (Lond) 335:632-635 (1988). In L6 myocytes, maximal reduction of glucose uptake has been reported at 10 pM. Ciaraldi, T. P., Cooper, G. J. S. & Stolpe, M., *Diabetes* 39:149A (1990) and Kreutter, D., Orena, S. J. & Andrews, G. C., *Diabetes* 39 (Suppl. 1): 121A (1990). These effects occur at the physiological concentrations of the hormone as measured and set forth in the below Examples.

Amylin also has been reported to produce marked effects on pathways of glucose metabolism in animals in vivo. In experiments utilizing the euglycemic, hyperinsulinemic glucose clamp, amylin reversed insulin-mediated suppression of hepatic glucose output in rats. Molina, J. M., Cooper, G. J. S., Leighton, B. & Olefsky, J. M., *Diabetes* 39:260-265 (1990) and Koopmans, S. J., vanMansfeld, A. D. M., Jansz, H. S., Krans, H. M. J., Radder, J. K., Frolich, M., deBoer, S. F., Kreutter, D. K., Andrews, G. C. & Maassen, J. A., *Diabetes* 39:101A (1990). Amylin also decreased peripheral uptake of glucose. Molina, J. M., Cooper, G. J. S., Leighton, B. & Olefsky, J. M., *Diabetes* 39:260-265 (1990), Koopmans, S. J., vanMansfeld, A. D. M., Jansz, H. S., Krans, H. M. J., Radder, J. K., Frolich, M., deBoer, S. F., Kreutter, D. K., Andrews, G. C. & Maassen, J. A., *Diabetes* 39:101A (1990) and Young, D. A., Deems, R. O., McIntosh, R. H., Deacon, R. W. & Foley, J. E., Diabetes 39 (Suppl. 1):116A (1990).

As noted above, glucagon owes its place in the treatment of hypoglycemia almost entirely to its ability to liberate glucose from the liver by initiating glycogenolysis through activation of liver phosphorylase. Its ability to accelerate gluconeogenesis, which is probably more important in glucose homeostasis, plays little part in this action, nor is glucagon reported to have significant effects upon peripheral glucose utilization (except possibly to accelerate it secondarily to glucagon-stimulated insulin secretion). The hyperglycemic effect of glucagon is abolished or diminished when, for any reason, the quantity of glycogen in the liver is reduced or is otherwise unavailable for conversion into glucose. V. Marks, "Glucagon in the Diagnosis and Treatment of Hypoglycemia," Chapter 55 of *Handbook of Experimental Pharmacology*, Vol. 66-II (Glucagon II) P. J. Lefebvre (Ed.) (Springer-Verlag 1983). In contrast, we have found the effect of amylin in increasing blood glucose is greatly diminished in fed animals (i.e., those having liver glycogen stores). On the other hand, we found that amylin was effective in increasing glucose levels in fasted animals, where glucagon had little or no effect. See FIG. 6.

The present invention provides for the co-administration of a glucagon compound together with amylin or an amylin agonist for the treatment of hypoglycemic conditions, especially those brought on by acute hypoglycemia such as insulin overdose or sulfonylurea overdose. The coadministration of amylin and a glucagon compound, for example, will allow a wider range of utility for the treatment of hypoglycemic incidents. Animals or patients undergoing a hypoglycemic reaction may be convulsing or comatose and their nutritional state may be unknown. Thus, the compositions of th present invention will act to alleviate hypoglycemia in patients having depleted or substantially diminished liver glycogen stores, as well as well-nourished patients having substantial liver glycogen stores and, thus, these compositions will be effective to raise blood glucose in all circumstances. As demonstrated in the below Examples, amylin is much more effective than glucagon in its hyperglycemic activity in treating animals in the fasted state, whereas glucagon has a much more effective hyperglycemic activity in treating fed animals where amylin elicits a lesser hypoglycemic response. Thus, the compositions of the present invention should beneficially extend the range and type of hypoglycemic episodes amenable to this hormonal therapy. (See e.g. FIG. 6).

In this regard, it will be noted that the amylin bolus injection experiments described in Example 1 below produced substantial and brisk increases in both plasma glucose and lactate. The hyperlactemia persisted for 1-2 hours and the hyperglycemia for 2-3 hours. These responses were associated with increased endogenous (hepatic) glucose production that persisted for 4-5 hours (compared to respective control groups). The significant increase of these responses over hypotensive controls indicate they result from a direct effect of amylin and not merely hypoperfusion. Similarly, the lack of measured differences in plasma catecholamines between treatment groups indicates that the observed effects were not caused by these agents. The observed excess of rates of glucose appearance over disposal leading to hyperglycemia with amylin occurred in spite of a prolonged fasting period In such a fasting period, liver glycogen would typically be depleted to 0.2% (wt/wt) in rats. Shulman, G. I., Rothman, D. L., Smith, D., Johnson, C. M., Blair, J. B., Shulman, R. G. & DeFronzo, R. A., *J. Clin. Invest.* 76:1229–1236 (1985).

Figure 2:
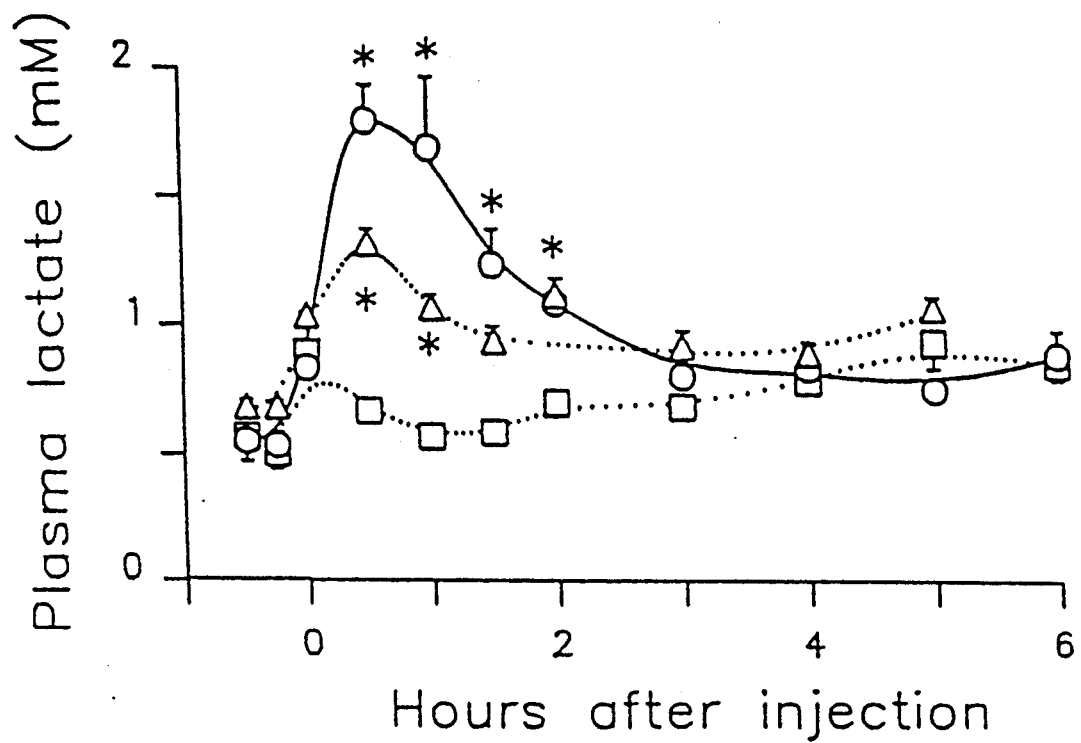
FIG. 2 shows the plasma lactate response (mean±SEM, n=6 for each curve) for groups described in FIG. 1. Symbols and asterisks have the same meaning as in FIG. 1.

White muscle in the rat exhibits increased lactate production in response to amylin in vitro. Leighton, B., Foot, E. A. & Cooper, G. J. S., *Diab. Med.* 6: Suppl. 2, A4 (1989). The observed appearance of lactate in the plasma following amylin administration in FIG. 2 is consistent with its originating from muscle glycogenolysis. The hepatic glucose production and plasma glucose are significantly elevated over control values for longer than is the plasma lactate. The sequence of observed effects is consistent with the determination that, following an amylin bolus, muscle lactate is released into the plasma and supplied to the liver where it serves as a substrate for gluconeogenesis. That is, amylin enhances Cori cycling.

The role of the Cori cycle in fuel homeostasis has been recently reevaluated. McGarry, J. D., Kuwajima, M., Newgard, C. B. & Foster, D. W., *Ann. Rev. Nutr.* 7:51–73 (1987). The widely accepted mechanism of hepatic glycogen repletion via "direct" glycogen synthesis (glucose to glucose-6-phosphate to glucose-1-phosphate to UDP-glucose to glycogen) was questioned (Radziuk, J., *Fed. Proc.* 41:110–116 (1982)) and isotope studies (Newgard, C. B., Hirsch, L. J., Foster, D. W. & McGarry, J. D., *J. Biol. Chem.* 258:8046–8052 (1983)) indicated that the majority of hepatic glycogen repletion occurred via an "indirect" gluconeogenic pathway. This was essentially confirmed by nuclear magnetic resonance tracing of $^{13}$C-labelled substrates. Shulman, G. I., Rothman, D. L., Smith, D., Johnson, C. M., Blair, J. B., Shulman, R. G. & DeFronzo, R. A., *J. Clin. Invest.* 76:1229–1236 (1985). The Cori cycle enables the bypassing of an impediment to direct glycogen synthesis, glucose to glucose-6-phosphate conversion via low affinity glucokinase. McGarry, J. D., Kuwajima, M., Newgard, C. B. & Foster, D. W., *Ann. Rev. Nutr.* 7:51–73 (1987). In the periphery, hexokinase catalyzes the reaction with a higher affinity.

The Cori cycle acts as a mechanism whereby metabolic fuel can exchange between high-capacity muscle stores and the liver, where it can be redirected into a variety of metabolic pathways as required. Lactate is released from muscle when glycolysis exceeds oxidative capacity, typically in association with accelerated muscle glycogenolysis. A hormone that continuously regulated this reaction would control the supply of lactate from the periphery to the liver, and hence rates of hepatic utilization. Amylin-mediated hyperlactemia is consistent with such a role for the hormone. The co-release of insulin plus amylin would therefore have an orchestrated effect on Cori cycle activity; insulin would regulate carbon flux into muscle stores while amylin would control its release. Combined hyperinsulinemia/hyperamylinemia would accelerate Cori cycling. Obese non-insulin dependent diabetic subjects, a group that has been reported to exhibit elevated plasma amylin/insulin concentrations (Ludvik, B., Svoboda, T., Hartter, E., Kuenburg, E., Brunnbauer, M., Woloszczuk, W. & Prager, R., *Diabetes* 39 (Suppl. 1), 116A (1990)), also show increased Cori cycle flux. Zawadski, J. K., Wolfe, R. R., Mott, D. M., Lillioja, S., Howard, B. V. & Bogardus, C., *Diabetes* 37:154–159 (1988); Consoli, A., Nurjahan, N., Capani, F. and Gerich, J., *Diabetes* 38:550–557 (1989).

While other studies have generally looked at amylin in regard to its ability to modulate insulin-mediated metabolic changes, somatostatin infusions were used as described below to inhibit endogenous insulin and glucagon secretion in determining the effects of amylin independent of changes in these hormones. A range of metabolic parameters following a single bolus dose of amylin was observed. The results herein are consistent with the conclusion that amylin has a role in controlling flux through the Cori (glucose to 3-carbon compound to glucose) cycle (Cori, G. T. & Cori, C. F., *J. Biol. Chem.* 131:297–298 (1939)) by modulating gluconeogenic substrate release from peripheral tissues and gluconeogenesis/glycogenolysis in the liver. Post-prandial flux through the Cori cycle appears to be a major mechanism of liver glycogen repletion. Newgard, C. B., Hirsch, L. J., Foster, D. W. & McGarry, J. D., *J. Biol. Chem.* 258:8046–8052 (1983).

In the studies described in Example 3, the effect of glucagon administration (at 0 hours) followed by a subsequent administration of amylin (6 hours) was observed in both fasted (20±1 hours) and fed rats. See FIG. 6 and Table I.

In fed rats, glucagon injection produced a rapid glycemic response that persisted for about 0.6 hrs. Glucagon is thought to exert its immediate effects through direct stimulation of hepatic glycogenolysis, which in man initially accounts for 85% of counter-regulatory hepatic glucose production. It has been reported that prolonged counter-regulatory hormone stimulation results in gluconeogenesis gradually replacing glycogenolysis as the mode of hepatic glycogenesis (Lecavalier, L. et al., *Am. J. Physiol.* 256:844–51 (1989)).

In contrast, there was a lesser glycemic response to glucagon in 20-hour fasted rats. In fasted rats, hepatic glycogen is minimal at 18–24 hours, being about 0.1–0.2% wt/wt. For this reason, it is said, "glucagon is helpful in hypoglycemia only if liver glycogen is available" and is of "little or no help in adrenal insufficiency, starvation or chronic hypoglycemia." (Eli Lilly and Company, "Information for the Physician." Glucagon for Injection USP Pamplet PA0866 AMP (1989)). Although hepatic glycogen content was not measured in this study, the data observed were consistent with hepatic glycogen depletion limiting glycogenesis following glucagon injection.

In fasted animals, amylin injection resulted in an abrupt increment in plasma lactate and a profound increase in plasma glucose that mirrored a relatively rapid decay in lactate. In fed animals there was an increase in plasma lactate approximately equal to that observed in fasted animals. However, compared to the fasted animals, there was a diminished glycemic response that was matched by a slower decay in plasma lactate.

Amylin is reported to have direct effects on skeletal muscle to stimulate glycogenolysis (Young, D. A., et al., *Am. J. Physiol.* 259:E457–E461 (1990)) and subsequent lactate output (Leighton, B., G. J. S. Cooper, *Nature* 335:632–635 (1988); Leighton, B. and E. Foot, *Biochem J.* 269:19–23 (1990)). It is probable that the hyperlactemia observed in the present study is derived from muscle glycogenolysis. Because amylin has been reported to reduce glucose uptake in rats both in vivo (Molina, J. M., et al., Diabetes 39:260-265 (1990); Koopmans, S. J., et al., Diabetes 39:101A (1990); Young, D. A., et al., Diabetes 39:116A (1990)), and in several in vitro muscle preparations (Leighton and Cooper, Nature 335:632-635 (1988); Kreutter, D., et al., Diabetes 39:121A (1990)), it is possible that it could have contributed to the hyperglycemia in the present study by blocking peripheral uptake of glucose. However, we have also previously shown that amylin increased endogenous glucose appearance in 20 hour fasted rats (Young et al., 1990). Total hydrolysis of extant hepatic glycogen expected in such animals (see. e.g., David, M., et al., J. Clin. Invest. 86:612-617 (1990); Goldstein, D. E., Metabolism 27;315-323 (1978)) could have accounted for no more than about 30% of the hyperglycemia observed in both that study and the presently reported study (estimated by immediate distribution of hepatic glucosyl moieties into the glucose space). We therefore believe that at least two thirds of the amylin-induced hyperglycemia in fasted rats is attributable to gluconeogenesis.

Optionally, amylin agonists may be used in place of amylin. Amylin agonists include non-human amylin species, such as rat amylin and dog amylin, and include peptides and peptide analogs (or mimicks) which exhibit amylin agonist activity and/or are chemically and structurally related to native amylin. Generally, useful amylin agonists exhibit an $EC_{50}$ of $\leq 500$ nanomoles/liter in the soleus muscle assay. Good amylin agonists have an $EC_{50}$ of $\leq 250$ nanomoles/liter. Particularly preferred amylin agonists have an $EC_{50}$ of $\leq 100$ nanomoles/liter.

Amylin agonists include compounds which are modifications of amylin. Amylin agonists include compounds having no 2,7-disulfide bridge, as well as those having alternate means for joining amino acids 2 and 7, including compounds having a 2,7-amide linkage such as cyclo$^{2,7}$[Asp$^2$, Lys$^7$] or having no 2,7-linkage at all, such as [Ser$^2$, Ser$^7$]-human amylin or [Ala$^2$, Ala$^7$]-human amylin. Other amylin agonists include those having a replacement amino acid at residue 23, [Xxx$^{23}$]amylin, and/or residue 29, [Xxx$^{29}$]amylin, wherein "Xxx" denotes one of the twenty naturally occurring amino acids or their D-isomers; such peptides include [Leu$^{23}$]amylin and [Pro$^{29}$]amylin. Other amylin agonists include compounds having deletions of the first or last amino acids such as $^{2-37}$-amylin or $^{1-36}$-amylin. Other amylin agonists include amylin precursors such as pre-proamylin (having a post-C terminal Gly or Gly, Lys) or compounds having additional amino acids at the N terminal end, including [Pro-NH] amylin and [Pro, Arg-NH-] amylin. Other amylin agonists include calcitonin gene-related peptides.

Such amylin agonists may be prepared by chemical modification of native amylin, by recombinant techniques or by conventional techniques used in peptide synthesis such as solid phase peptide synthesis using an automated peptide synthesizer.

The products of this invention may be made available in lyophilized dosage unit form and will generally be administered in the same manner as glucagon, i.e., parenterally or by infusion. Since their structure and activity is similar to glucagon they will generally be administered with the same types of pharmaceutically acceptable excipients as glucagon. Amylin, or an amylin agonist, may in fact be co-administered with glucagon in the same dosage units. These amylin agonists may also be administered simultaneously with glucagon or a glucagon compound but in separate pharmaceutical compositions.

Since the products of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared form both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided for as parenteral compositions for injection or infusion. They can, for example be suspended in an inert oil, suitably a vegetable oil such as sesame, peanut, or olive oil. Alternatively they can be suspended in an aqueous isotonic buffer solution at a pH of about 5.6 to 7.4 . Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired the solutions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of glucagon and/or an amylin agonist which will be effective in one or multiple doses to control blood sugar at the selected level. As will be recognized by those in the field, an effective amount of therapeutic agent will vary with many factors including the age and weight of the patient, the patient's physical condition, the blood sugar level to be obtained, and other factors. Typical dosage units will contain from about 0.1 to 10 mg of amylin or the amount of amylin agonist to have that effect and about 0.1 to about 1.0 mg of glucagon, (or an amount of glucagon compound to have that effect) although wide variations from this range are possible while yet achieving useful results.

The following Examples are illustrative, but not limiting of the methods and compositions of the present invention. Other suitable compounds that may be modified or adapted for use are also appropriate and are within the spirit and scope of the invention.

EXAMPLE 1

Each treatment of the experimental design used 6 male Harlan Sprague Dawley rats (body mass 388±7 g, age 93±2 days). Animals were housed at 22.7°±0.8° C. in a 12:12 hour light:dark cycle (experiments being performed during the light cycle) and fed and watered ad libitum (Diet LM-485, Teklad, Madison, Wis.). Animals were overnight fasted (13.3±2.8 hours before surgery). Anesthesia was induced with 5% halothane, maintained at 2% during surgery and at 0.8–1% during metabolic recordings. Tracheotomy and cannulation of right femoral artery and vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The femoral venous line was used for acute (bolus) injections.

A 4-limb ECG was monitored via an ECG/biotach amplifier (Model 13-4615-65A, Gould, Cleveland, Ohio) and heart rate derived.

Colonic temperature was measured using a thermistor probe and controller (Model 73A, YSI, Yellow Springs, Ohio) which provided closed-loop control of core temperature by switching a heated operating table.

The endotracheal tube was connected to a specially constructed pneumotach which measured the pressure differential across a small constriction in the tracheal flow. The output was linearized on-line to flow using a calibration table (Labtech Notebook function). A sample of the tracheal flow was continuously analyzed for $N_2$, $O_2$, Ar, $CO_2$, water vapor and halothane using a respiratory mass spectrometer (MGA 3000, Airspec, Biggin Hill, Kent, England).

Signals for tracheal flow, $O_2$ and $CO_2$ concentration, heart rate, arterial pressure and colonic temperature were periodically sampled and stored with 12-bit precision at 20 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp, Wilmington, Mass.). Gas tension and flow signals were synchronized and used to derive oxygen consumption rates and respiratory quotient over 30-second epochs. Upon cannulation, animals were infused with heparinized saline containing somatostatin (S-9129, Sigma, St Louis, Mo.), 3.4 nmol/hr and 3-[$^3$H]-glucose (New England Nuclear/DuPont, Wilmington, Del.), 44.4 kBq/hr.

There were three treatment groups:

(1) Amylin Bolus (n=6): After 2-hours infusion, animals were injected with a 100ml bolus of saline containing 25.5 nmol freshly dissolved rat amylin (lot#ZG485, Bachem, Torrance, Calif.). Bioactivity of peptide to be used in this study was first verified using a soleus muscle-based assay (Leighton, B. and Cooper, G. J. S., Nature 335:632–635 (1988) ($EC_{50}$=6.7±1.5 nM).

(2) Peptide Controls (n=6): Instead of fresh amylin, rats were injected with either 25.5 nmol of the same peptide autoclaved at 121° C. for 90 minutes (n=3) or saline alone (n=3). Since there were no differences between responses to either autoclaved amylin or saline, data have been pooled into a single control group referred to as "peptide controls".

(3) Blood Pressure Controls (n=6): Instead of fresh amylin, 18 nmol pulses of phentolamine in 50 $\mu$l of saline were injected via the femoral venous cannula in a schedule calculated to mimic the transient hypotensive profile produced by the 66 nmol/kg amylin bolus.

Arterial samples were drawn 0.5, 0.25 and 0 hr before bolus injection, and 0.5, 1, 1.5, 2, 3, 4, 5 and 6 hr after injection. Samples were collected into $Na_2$.EDTA (final concentration approximately 5 mM), and separated plasma analyzed for glucose, lactate, tritiated glucose, insulin and rat amylin.

Glucose and lactate were analyzed by immobilized enzyme chemistries (glucose oxidase, L-lactate oxidase, Analyzer model 2300-STAT, YSI, Yellow Springs, Ohio).

Tritiated glucose specific activity was determined after counting the tritium remaining after evaporation of plasma previously stripped of protein by perchloric acid precipitation. Best, J. D., Judzewitsch, Pfeiffer, M. A., Beard, J. C., Halter, J. B. & Porte, D., *Diabetes* 31:333–338 (1982). With steady infusion rates of radioglucose (44.4 kBq/hr), rates of endogenous glucose production were determined from tritiated glucose specific activity and an assumed glucose space using a modification (Proietto, J., Rohner-Jeanrenaud, F., Ionescu, E., Terretaz, J., Sauter, J. F. & Jeanrenaud, B., *Am. J. Physiol.* 252:E77–E84 (1987)) of Steele's non-steady-state tracer dilution method. Steele, R., *Ann. NY Acad. Sci.*, 8:420–430 (1959).

Insulin was determined by radioimmunoassay (Micromedic human insulin RIA kit, ICN Biomedicals, Horsham, Pa.), sensitivity 6 pM, cross-reactivity to rat insulin 89.5%. Rat amylin was determined by radioimmunoassay (Kit RIK7323, Peninsula Laboratories, Belmont, Calif.) following C-18 resin extraction and elution with 80% acetonitrile/0.1% trifluoroacetic acid.

Plasma catecholamines (epinephrine and norepinephrine) were measured at 0, 2, 4 and 6 hours post-injection using HPLC with electrochemical detection following plasma extraction with alumina. A modification of the method of Weicker et al. (Weicker, H., Feraudi, M., Hagle, H. & Pluto, R., *Clin. Chim. Acta* 141:17–25 (1984)), whereby internal standard (dihydroxybutyric acid) was added to plasma prior to extraction enabled analysis of 50 $\mu$L samples with a coefficient of variation of 7.8%.

Statistical analyses were by Student's t-test routines contained in the SYSTAT system (Systat, Evanston, Ill.) using $p<0.05$ as the level of significance. Unless stated otherwise, all results are reported as means± standard error of the mean.

Measured blood glucose and lactate levels are shown in FIGS. 1 and 2. Following injection of amylin (66 nmol/kg) there was a rapid increase in plasma glucose from 5.9+0.3 mM to 11.0+0.6 mM glucose. In contrast, prolonged experimental conditions produced a slower, sustained rise in plasma glucose in control animals. Amylin treated rats (group 1) remained significantly hyperglycemic relative to inactive-peptide controls (group 2) for at least 3 hours, and relative to the blood pressure controls for at least 2 hours. FIG. 2 shows that plasma lactate concentration had increased 230% by 30 minutes after injection and remained significantly elevated for at least 2 hours.

There was a significant fall in mean arterial pressure following 2 hours somatostatin infusion from 101±2 to 83±5 mmHg, (13.47±0.27±11.07 0.67 kPa, P<0.01). In addition, with the bolus amylin injection, there was a further fall in mean arterial pressure that was complete within about 60 seconds. Blood pressure was still significantly lower (73 versus 91 mmHg) and heart rate significantly higher (336 versus 320 beats/min) in the amylin injected group 30 minutes post injection but both had returned to peptide control levels (group 2) by 60 minutes post-injection (see FIG. 3B).

The blood pressure control group (group 3) was designed to replicate the change in arterial pressure produced by the vasoactivity of this large dose of amylin in the presence of a somatostatin infusion, and thereby gauge the component of the hyperglycemia and hyperlactemia that might be attributable to reduced tissue perfusion resulting from reduced arterial pressure.

Figure 3A:
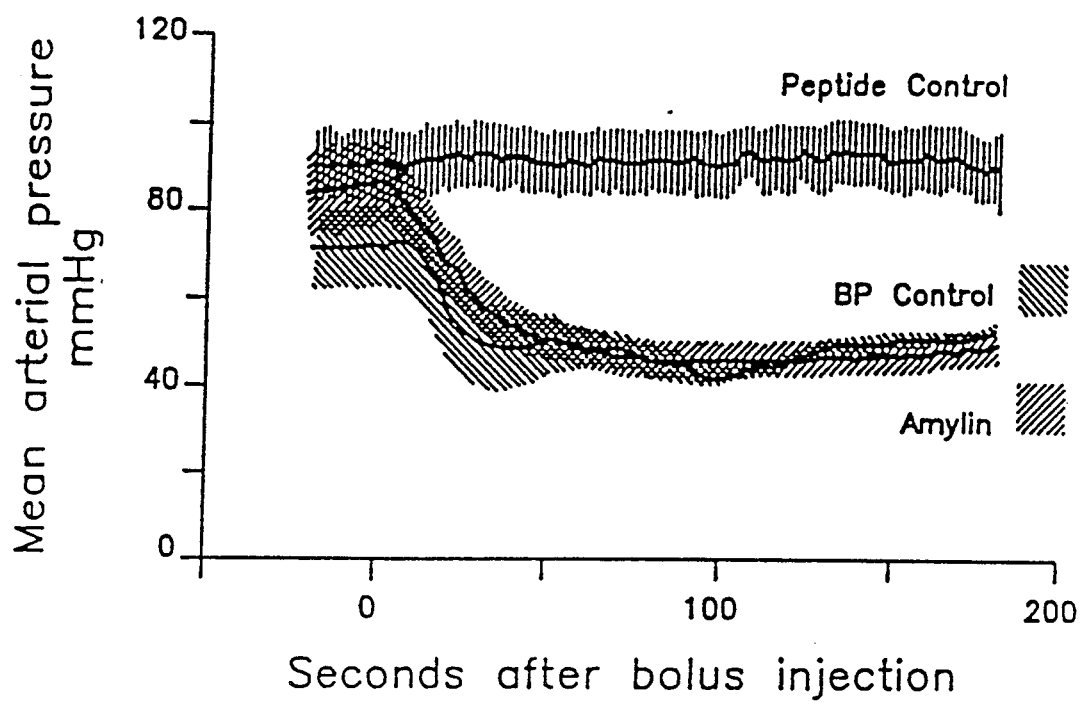
FIG. 3A shows the mean arterial blood pressure response (2-second means±S.E. indicated by shading) for rats injected with amylin (66 nmol/kg), peptide control or phentolamine in a schedule designed to replicate the amylin blood pressure response. Subacute blood pressure response is shown in FIG. 3B as mean arterial pressure (30-second means±S.E.). Symbols, error bars and asterisks have the same meaning as in FIG. 1. In addition, the acute blood-pressure response is plotted at the time of injection.
Figure 3B:
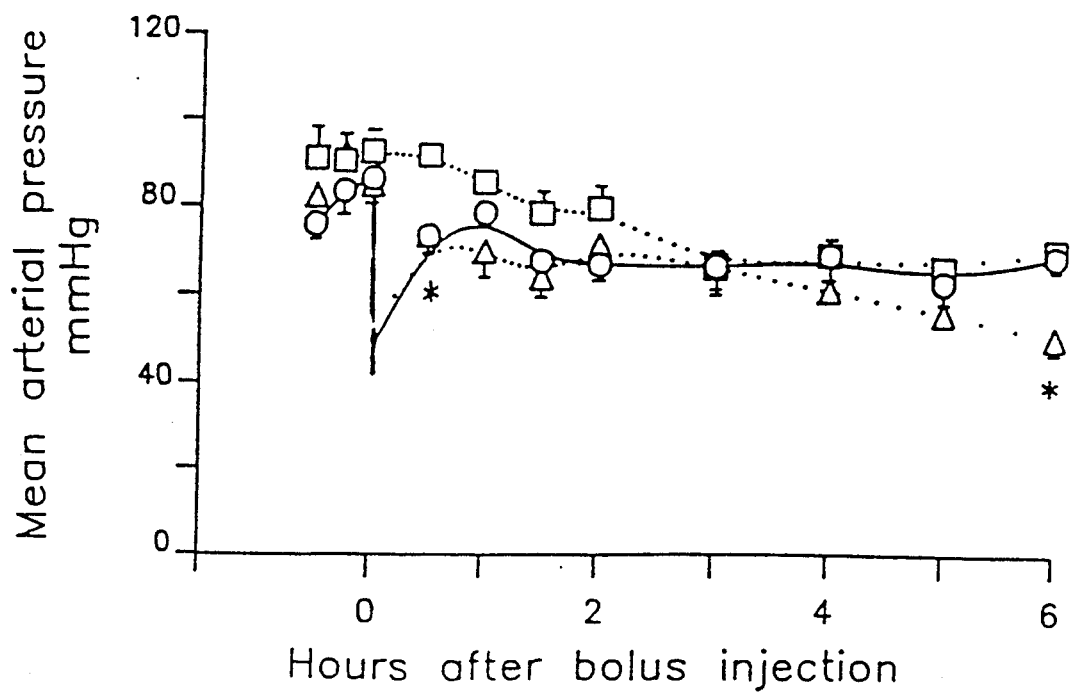

Over the 6 hour post-injection period, there were no significant differences in mean arterial pressure between amylin-and phentolamine-treated groups. FIG. 3A illustrates the arterial pressure response to repetitive pulses of 18 nmol of phentolamine in comparison to the target (group 1) pressure profile. In this group there was an increased glucose and lactate response over the normotensive controls. However, it was not as great and had a clearly different temporal profile to the amylin response shown in FIGS. 1 and 2.

Blood catecholamine (norepinephrine) levels did not differ in any of the treatment group comparisons (amylin treated versus peptide controls; amylin treated versus blood pressure controls; peptide controls versus blood pressure controls) at any of the 4 time points (0, 2, 4, 6 hours post-injection), except on one occasion (peptide control value > amylin treated group at 2 hours). In neither a pooled data set from all 3 treatment groups nor from just the hypotensive groups (amylin treated + blood pressure controls), was there a significant increment in norepinephrine over pre-injection levels. Epinephrine levels, analyzed in the same way showed no significant differences at any time point for any comparison, and no increment with time in pooled data sets. Plasma norepinephrine levels were $3.9\pm0.4$, $5.1\pm0.6$, and $3.9\pm0.3$ nM, and plasma epinephrine levels were $4.1\pm0.9$, $3.7\pm0.4$, and $5.5\pm0.8$ nM in amylin-treated, peptide control and blood pressure control groups respectively.

With regard to blood insulin levels there was no change in plasma insulin concentration from the pre-injection level in any of the treatment groups over the duration of the experiment, indicating that somatostatin had effectively inhibited any hyperinsulinemia that may have been expected from the observed hyperglycemic episodes. Similarly, there was no difference between treatment groups at any of the time points throughout the experiment (0, 2, 4, 6 hours). Glucose-stimulated insulin secretion was effectively inhibited by somatostatin infusion to ensure that glucagon secretion was inhibited as well. Gerich, J. E., Lorenzi, M., Schneider, V., Kwan, C. W., Karam, J. H., Guillemin, R. & Forsham, P. H., *Diabetes* 23:876-880 (1974). Plasma insulin levels were $128\pm21$, $184\pm22$, and $153\pm15$ pM in the amylin-treated, peptide control and blood pressure control groups respectively.

Isotopically determined endogenous glucose production in the amylin injected group increased to 214% and 219% of the corresponding control values at 1 and 2 hours post-injection respectively, and remained significantly elevated (compared to both the peptide controls and to the pre-injection level) for 4 hours. Amylin injection resulted in an initial rate of increase in plasma glucose concentration of 0.12 mM/min. When distributed throughout the estimated glucose space (97 ml), this converts to an excess of glucose appearance over glucose disappearance of 11.3 $\mu$mol/min. This increase represents an approximate doubling of the resting rate of glucose production over that measured in controls (13.5 $\mu$mol/min).

Figure 4:
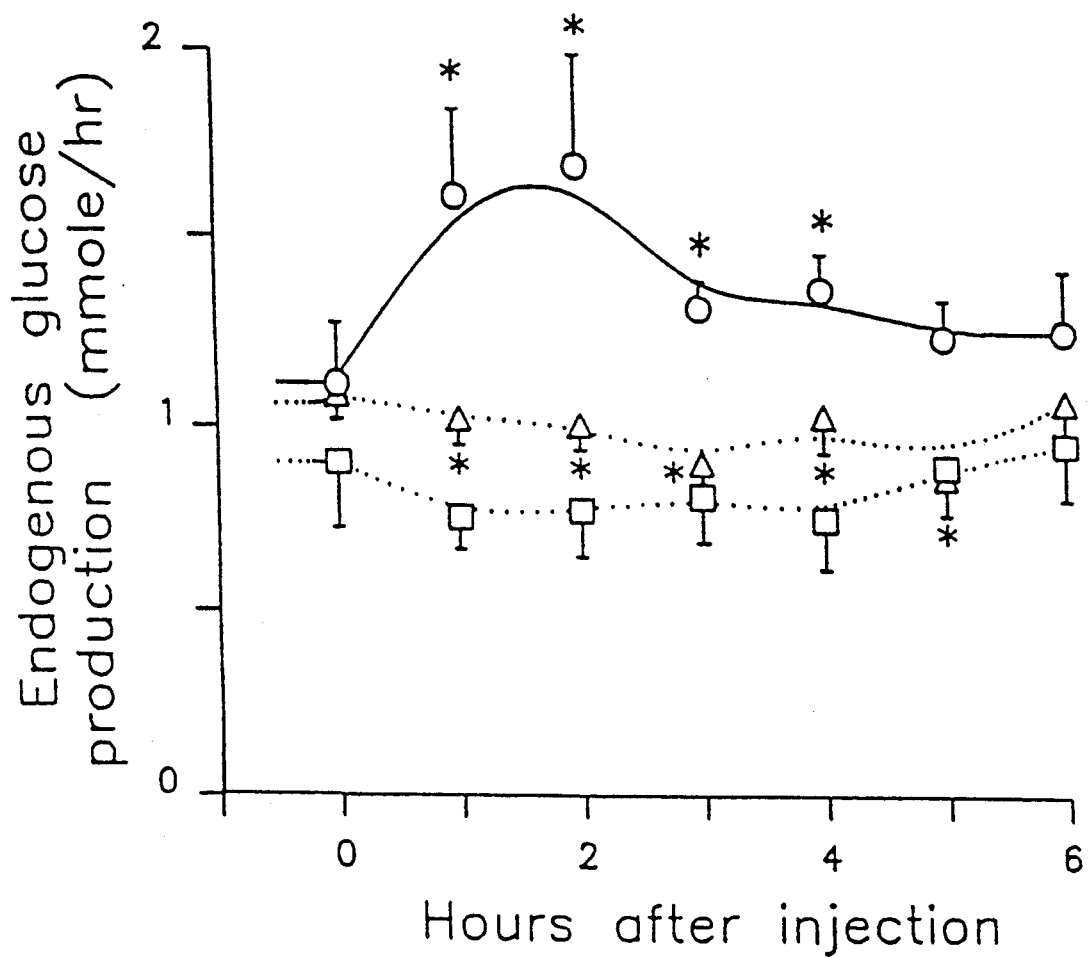
FIG. 4 shows isotopically determined, non-steady-state endogenous (hepatic) glucose production in rats injected intravenously with 25.5 nmol amylin (open circle), peptide control (open square) or phentolamine as described for the above figures (open triangle). Sample numbers and the meaning of symbols, bars and asterisks are the same as in FIGS. 1 and 2.

Similarly, endogenous glucose production in the amylin injected group remained significantly elevated compared to the blood pressure controls for 5 hours post injection. As shown in FIG. 4, the control groups did not differ from each other at any time point.

Rates of oxygen consumption did not change over the course of the experiment in either the experimental or peptide control group. Nor were they different between groups ($7.89\pm0.38$ and $7.44\pm0.34$ ml/min respectively pre-injection, versus $7.82\pm0.55$ and $7.32\pm0.26$ ml/min at the time of peak glycemic response [1 hour post-injection]).

Respiratory quotients (RQ) after overnight fasting were near the theoretical minimum after overnight fasting in amylin treated animals ($0.720\pm0.014$) and peptide controls ($0.747\pm0.018$). There were no changes in RQ from pre-injection values following amylin injection, and no differences between amylin treated and peptide control groups.

EXAMPLE 2

In this Example the effects of amylin and glucagon on plasma glucose and lactate in fasted, anesthetised rats were compared.

Sixteen male Harlan Sprague Dawley rats were housed at $22.7°\pm0.8°$ C. in a 12:12 hour light:dark cycle (experiments being performed during the light cycle) and fed and watered ad libitum (Diet LM-485, Teklad, Madison, Wis.). Animals were overnight fasted prior to experimentation. Anesthesia was induced with 5% halothane, maintained at 2% during surgery and at 0.8-1% during metabolic recordings. Tracheotomy and cannulation of right femoral artery and vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The femoral venous line was used for acute (bolus) injections. A 4-limb ECG was monitored via an ECG-/biotach amplifier (Model 13-4615-65A, Gould, Cleveland, Ohio) and heart rate derived.

Colonic temperature was measured using a thermistor probe and controller (Model 73A, YSI, Yellow Springs, Ohio) which provided closed-loop control of core temperature by switching a heated operating table. Signals for heart rate, arterial pressure and colonic temperature were periodically sampled and stored with 12-bit precision at 20 Hz using a computerized data acquisition system (DT2801A A/D converters, Data-Translation, Marlboro, Mass.; AST Premium 386 computer, AST Research, Irvine, Calif.; Labtech Notebook software, Laboratory Technologies Corp, Wilmington, Mass.).

There were three treatment groups:
1. Amylin Bolus (n=6; mass=$310\pm7$g; age=$110\pm2$d; fasted $20.0\pm0.7$hr). After 2-hours infusion, animals were injected with a 100 $\mu$l bolus of saline containing 25.5 nmol freshly dissolved rat amylin (lot#ZG485, Bachem, Torrance, Calif.). Bioactivity of peptide to be used in this study was first verified using the soleus muscle-based assay ($EC_{50}=6.7\pm1.5$ nM).

2. Glucagon Bolus (n=6; mass=331±5g; age=76±1d; fasted 18.7±0.4hr; structures of rat and human glucagon are identical). After 2-hours infusion and taking of basal samples, animals were injected with 28.7 nmol glucagon in a 100 μl bolus of diluent (Glucagon for injection USP, Eli Lilly and Company, Indianapolis, Ind.; lot#4MC51D, contains glucagon 1 mg, lactose 49 mg constituted into 1 ml aqueous solution of 1.6% glycerin and 0.2% phenol). Following 6 hours observation of the glucagon response, 25.5 nmol of rat amylin (as per group 1) was injected and the response followed for a further 2 hours.

3. Controls (n=3; mass=354±17g; age=82±1d; fasted 19.5±0.7hr). Control animals were injected with saline alone.

Arterial samples were drawn 0.5, 0.25 and 0 hr before bolus injection, and 0.5, 1, 1.5, 2, 3, 4, 5, 6 hr after injection (group 1), and at 6.5, 7, 7.5 and 8 hours (group 2). Arterial samples were collected into heparinized capillaries and separated plasma analyzed immediately for glucose and lactate using immobilized enzyme chemistries (glucose oxidase, L-lactate oxidase, Analyzer model 2300-STAT, YSI, Yellow Springs, Ohio). Statistical analyses were by Student's t-test routines contained in the SYSTAT system (Systat, Evanston, Ill.). Unless stated otherwise, all results are reported as means ±standard error of the mean.

Figure 5A:
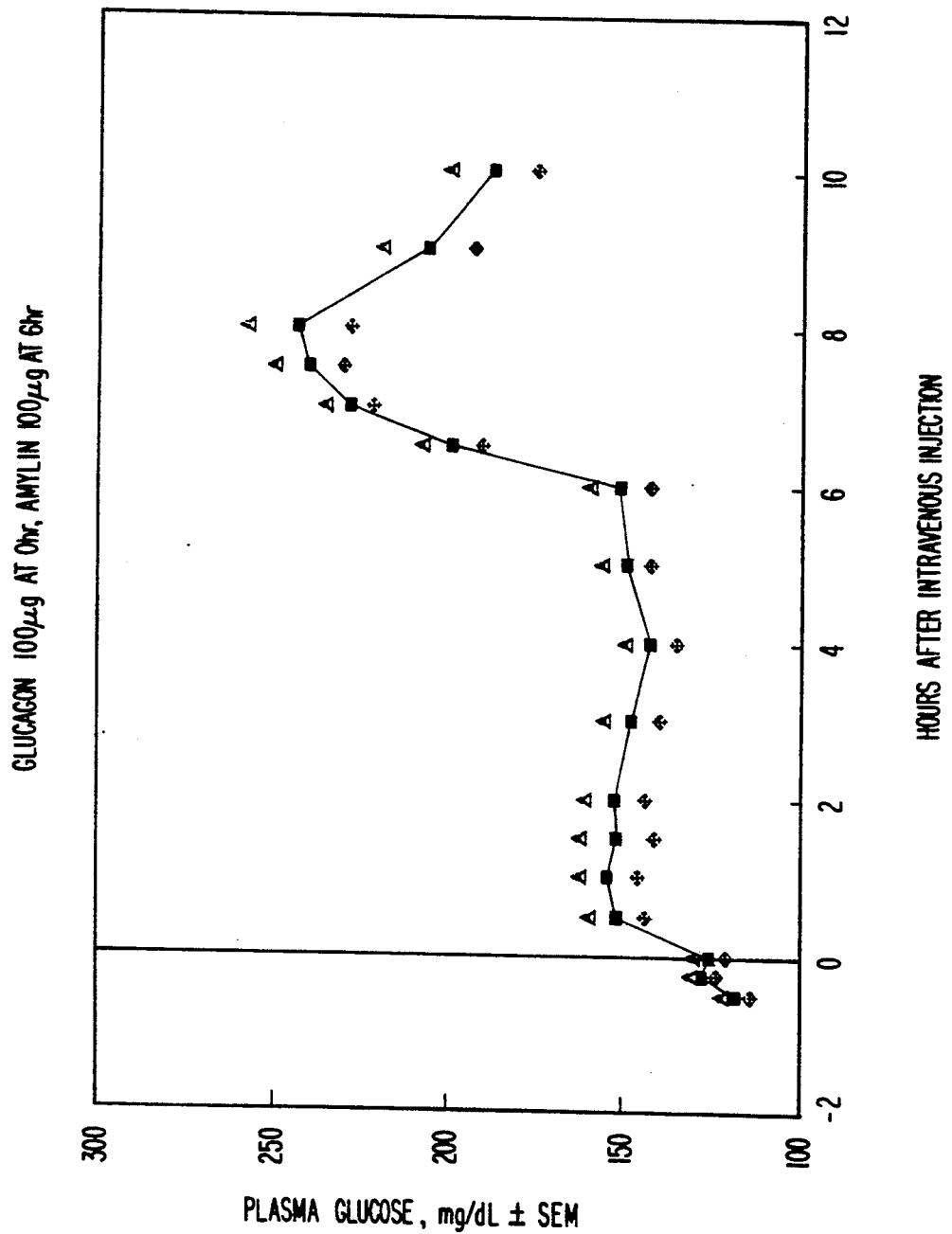

Results are plotted in FIG. 5A and 5B. Amylin injection (i.v. bolus of 25.5 nmol) resulted in a rapid increase in both plasma glucose and lactate. Elevations of plasma glucose above control were significant at 30 minutes and persisted beyond 2 hours. The peak glycemic response occurred at 1.50±0.22 hours and represented a 5.59±0.46 mM increment above preinjection levels. Plasma lactate levels peaked within 30 minutes of injection, with a 136% increment of 1.02±0.11 mM over preinjection levels of 0.75±0.06 mM (increment vs control, $p<0.001$).

Glucagon injections (i.v. bolus of 28.7 nmol) resulted in a peak glycemic response of 1.94±0.34 mM which occurred 1.58±0.24 hours after i.v. injection (see FIG. 5A). The glycemic response to glucagon was less than to either of the amylin responses (35% of the amylin-alone response, $p<0\,001$: 35% of the amylin-after-glucagon response, $p<0.003$). Compared to control animals, there was negligble increment in plasma lactate with glucagon (0.09±0.04 mM) (see FIG. 5B).

Six hours after glucagon injection, amylin (i.v. bolus of 25.5nmol) resulted in a glycemic response of 5.60±0.86 mM, peaking 1.67±0.17 hours post-injection, and a brisk lactate response of 3.44±0.42 mM, peaking within 30 min of injection (see FIG. 5A and 5B). The magnitude of the amylin-induced lactate response following glucagon was 3.4 times greater than that with amylin alone ($p<0.001$). The magnitudes of the glycemic responses were almost identical ($p=0.99$).

The $t_\frac{1}{2}$ for the decline of amylin-generated glucose were 175 and 59 minutes for amylin alone and amylin after glucagon respectively. The corresponding values for lactate were 55 and 34 minutes. There were no significant differences in mean arterial pressure comparing amylin alone versus control, amylin alone versus glucagon or amylin alone versus amylin after glucagon for any of the comparable time points before and after injection.

EXAMPLE 3

In this Example the effects of glucagon administration (0 hours) followed by amylin administration (6 hours) on plasma glucose and lactate in fed and fasted (20±1 hours) rats was compared.

Male Harlan Sprague Dawley rats were housed at 22.7°±0.8° C. in a 12:12 hour light:dark cycle (experiments being performed during the light cycle) and fed and watered ad libitum (Diet LM-485, Teklad, Madison, Wis.). Fasted animals were deprived of food 20±1 hours prior to experimentation. Fed animals were allowed access to food until surgery. Anesthesia was induced with 5% halothane, maintained at 2% during surgery and at 0.8-1% during metabolic recordings. Tracheotomy and cannulation of the right femoral artery and saphenous vein were performed.

The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. All chronically infused agents were added to this infusate. The venous line was used for acute (bolus) injections.

A 4-limb ECG was monitored via an ECG/biotach amplifier (Model 13-4615-65A, Gould, Cleveland, Ohio) and heart rate derived.

Colonic temperature was measured using a thermistory probe and controller (Model 73A, YSI, Yellow Springs, Ohio) which provided closed-loop control of core temperature by switching a heated operating table.

Signals for heart rate, arterial pressure and colonic temperature were periodically sampled and stored with 12-bit precision at 20 Hz using a computerized data acquisition system (DT2801A A/D converters, Data-Translation, Marlboro, Mass.; AST Premium 386 computer, AST Research, Irvine, Calif.; Labtech Notebook software, Laboratory Technologies Corp., Wilmington, Mass.).

There were two treatment groups.

1. Glucagon Bolus+Amylin Bolus, Fasted (n=6; mass-331±5 g; age=76±1 day; fasted 18.7±0.4 hours). Structures of rat and human glucagon are identical. After 2-hours infusion and taking of basal samples, animals were injected with 86.4 nmol/kg glucagon in a 100 μl bolus of diluent (Glucagon for injection USP, Eli Lilly and Company, Indianapolis, Ind.; lot#4MC51D, contains glucagon 1 mg , lactose 49 mg constituted into 1 ml aqueous solution of 1.6% glycerin and 0.2% phenol). Following 6 hours observation of the glucagon response, 76.8 nmol/kg of rat amylin (as per group 1) was injected and the response followed for a further 4 hours.

2. Glucagon Bolus+Amylin Bolus, Fed (n=9; mass=322±11 g; age=63±3 day; fasted 0 hour). Other than having continued access to food, these animals were treated identically to those in group A.

Arterial samples were drawn 0.5, 0.25 and 0 hour before bolus injection, and 0.5, 1, 1.5, 2, 3, 4, 5, 6, 6.5, 7, 7.5, 8, 9 and 10 hours after injection. Arterial samples were collected into heparinized capillaries and the separated plasma analyzed immediately for glucose and lactate using immobilized enzyme chemistries (glucose oxidase, L-lactate oxidase, Analyzer model 2300-STAT, YSI, Yellow Springs, Ohio). The packed red cells were reinfused to minimize loss of red cell mass.

Plasma was collected for insulin measurement every 2 hours. Insulin was determined by radioimmunoassay (Micromedic human insulin RIA kit, ICN Biomedicals, Horsham, Pa.) with a sensitivity of 6 pM and a cross-reactivity to rat insulin of 89.5%.

Figure 6:
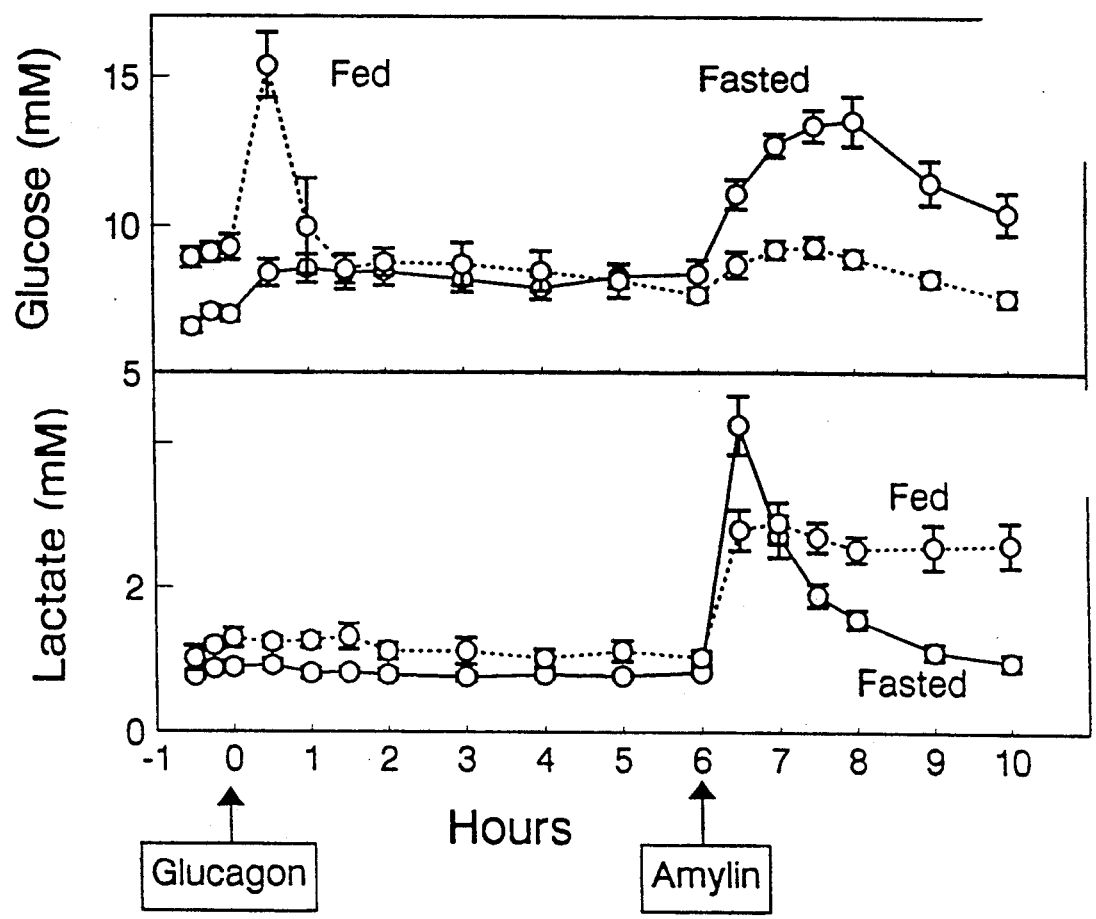
FIG. 6 shows the effects of an intravenous injection of 100 micrograms glucagon (0 hours) followed by an intravenous injection of 100 micrograms amylin (6 hours) on plasma arterial levels of glucose and lactate in (—O —) fed and (—O—) fasted (20±1 hour) rats.

In 20-hour fasted rats, glucagon injections resulted in a peak glycemic response of 1.94±0.34 mM which occurred 1.58±0.24 hours after i.v injection (see FIG. 6). The glycemic response to glucagon was less than that observed with either amylin alone (35% of that response, $P<0.001$) or with amylin subsequently injected into the same animals (35% of group 1 amylin response, $P<0.003$). Compared to control animals, there was no significant increment in plasma lactate with glucagon (0.09±0.04 mM; $P=0.06$). In the glucagon injected group, there was a significant elevation of mean arterial pressure ($P<0.05$) and heart rate ($P<0.05$) consistent with its reported inotropic and chronotropic effects.

Six hours after glucagon injection into fasted rats, amylin resulted in an increase in plasma glucose of 5.60±0.86 mM above the prevailing levels of s.37±0.48 mM, peaking 1.67±0.27 hours post-injection, almost identical to the pattern observed with amylin alone. There was also a brisk lactate response of 3.44±0.42 mM (3.4 times greater than in amylin alone) the decline in amylin-generated lactate in the fasted group was 34 minutes. There were effects on arterial pressure similar to those observed in rats injected with amylin alone.

In contrast to the fasted animals (group 1), fed animals showed a brisk glycemic response to intravenous glucagon (see FIG. 6). The increment in plasma glucose was 6.29±0.92 mM above preinjection levels. However, compared to the more prolonged hyperglycemia produced by amylin, the glycemic response to glucagon relative to controls lasted only 0.6 hr. As in fasted animals (group 1), glucagon was not associated with a significant increase in plasma lactate (30 minute increment 0.07±0.08 mM, ns).

Amylin administered 6 hours later into these same fed rats resulted in a lactemic response 56% of that produced in fasted rats (lactate increment 1.92±0.22 mM, group 2 vs. group 1, $P<0.05$). The increase in plasma glucose was diminished compared to that observed in fasted rats (2-hour glucose increment 1.76±0.37 mM, group 2 response=31% group 1 response, $p<0.01$). The plasma lactate remained higher for longer in the fed rats ($t\frac{1}{2}=138$ min.) compared to the fasted rats. Plasma insulin levels for groups 1 and 2 are compared in Table I. Levels were approximately 5 times higher in the fed animals than in the fasted animals.

TABLE I

| | Insulin Levels (pM) in Fasted and Fed Rats | | |
|---|---|---|---|
| Time (hours) | Fasted (group 1) | Fed (group 2) | p |
| 0 (pre-glucagon) | 46.2 ± 3.6 | 279.6 ± 94.8 | <0.03 |
| 2 | 43.8 ± 4.2 | 232.8 ± 65.4 | <0.01 |
| 4 | 58.8 ± 9.0 | 310.8 ± 48.0 | <0.001 |
| 6 (pre-amylin) | 45.0 ± 2.4 | 197.4 ± 19.2 | <0.001 |

EXAMPLE 4

In this example, amylin agonist activity in a soleus muscle-based assay (Leighton, B. and Cooper, G. J. S., Nature 335:632-635 (1988)) was measured.

Results are reported in Table II.

TABLE II

| ACTIVITY OF AMYLIN AGONISTS | |
|---|---|
| Peptide | ED$_{50}$ in Soleus Muscle Assay |
| cyclo$^{2,7}$[Asp$^2$,Lys$^7$]-Human Amylin | 22.96 nM ± 0.18 log unit |
| [Pro$^{29}$]-Human Amylin | 11 nM ± 0.10 log unit |

TABLE II-continued

| ACTIVITY OF AMYLIN AGONISTS | |
|---|---|
| Peptide | ED$_{50}$ in Soleus Muscle Assay |
| [Leu$^{23}$]-Human Amylin | 94.48 nM ± 0.19 log unit |

Although the invention has been described with respect to specific embodiments, uses and methods, it will be appreciated that various changes and modifications may be made without departing from the invention.

What is claimed is:

1. A composition comprising glucagon and an amylin admixed in a form suitable for therapeutic administration.

2. A composition comprising a glucagon compound and an amylin agonist admixed in a form suitable for therapeutic administration.

3. The composition of claim 1 wherein said amylin is rat amylin.

4. The composition of claim 2 wherein said amylin agonist is a calcitonin gene-related peptide.

5. The composition of any of claims 1, 2 or 3 which is in lyophilized dosage unit form.

6. A method for enhancing glucose levels in a mammal, which comprises the administration of a therapeutically effective amount of the composition of any of claims 1, 2, 3 or 4.

7. A method for the treatment of acute hypoglycemia in mammals, which comprises the administration of a therapeutically effective amount of the composition of any of claims 1, 2, 3 or 4.

8. The method of claim 6 wherein said administration is by parenteral injection.

9. The method of claim 7 wherein said administration is by parenteral injection.

10. The method of claim 6 wherein said administration is by intravenous infusion.

11. The method of claim 7 wherein said administration is by intravenous infusion.

12. A method for the control of hypoglycemic conditions in mammals, which comprises the co-administration of therapeutically effective amounts of a glucagon compound and an amylin agonist.

13. The method of claim 12 wherein said amylin agonist is amylin.

14. The method of claim 12 wherein said amylin agonist is a calcitonin gene-related peptide.

15. A method for the treatment of acute hypoglycemia in mammals, which comprises the co-administration of therapeutically effective amounts of a glucagon compound and an amylin agonist.

16. The method of claim 15 wherein said amylin agonist is amylin.

17. The method of claim 15 wherein said amylin agonist is a calcitonin gene-related peptide.

18. The composition of claim 1 wherein said amylin is human amylin.

19. The composition of claim 2 wherein said amylin agonist comprises an amylin having a proline residue at amino acid position 29.

20. The composition of claim 2 wherein said amylin agonist comprises an amylin having a leucine residue at amino acid position 23.

21. The method of claim 12 wherein said amylin agonist comprises an amylin having a proline residue at amino acid position 29.

22. The method of claim 15 wherein said amylin agonist comprises an amylin having a proline residue at amino acid position 29.

23. The method of claim 12 wherein said amylin agonist comprises an amylin having a leucine residue at amino acid position 23.

24. The method of claim 15 wherein said amylin agonist comprises an amylin having a leucine residue at amino acid position 23.

* * * * *